US00PP34936P2

(12) United States Plant Patent
Ackerman et al.

(10) Patent No.: US PP34,936 P2
(45) Date of Patent: Jan. 24, 2023

(54) STRAWBERRY PLANT NAMED 'PE-11.2175'

(50) Latin Name: ***Fragaria* x *ananassa***
Varietal Denomination: PE-11.2175

(71) Applicant: Plant Sciences, Inc., Watsonville, CA (US)

(72) Inventors: Stephen M. Ackerman, Salinas, CA (US); Steven D. Nelson, Watsonville, CA (US); Michael D. Nelson, Watsonville, CA (US); Daniel S. Nelson, Watsonville, CA (US)

(73) Assignee: Plant Sciences, Inc., Watsonville, CA (US)

( * ) Notice: Subject to any disclaimer, the term of this patent is extended or adjusted under 35 U.S.C. 154(b) by 0 days.

(21) Appl. No.: 17/879,137

(22) Filed: Aug. 2, 2022

(51) Int. Cl.
*A01H 6/74* (2018.01)
*A01H 5/08* (2018.01)

(52) U.S. Cl.
USPC ..... Plt./209

(58) Field of Classification Search
USPC ..... Plt./209
See application file for complete search history.

(56) References Cited

U.S. PATENT DOCUMENTS

PP17,312 P2 12/2006 Ackerman et al.
PP28,756 P3 12/2017 Ackerman et al.

*Primary Examiner* — Annette H Para
(74) *Attorney, Agent, or Firm* — Foley & Lardner LLP

(57) ABSTRACT

This invention relates to a new and distinct variety of strawberry plant named 'PE-11.2175'. This new strawberry plant named 'PE-11.2175' is primarily adapted to the growing conditions of the central coast of California, and is primarily characterized by its orange red fruit color, small fruit size, and conical fruit shape; fair fruit flavor, medium to soft flesh, with seeds typically held level with to below the surface; large plant size, semi-upright, with medium to dense density and strong vigor; medium to light green foliage color, large foliage size and slightly to strongly convex in cross section; and fruiting trusses typically held beneath the foliage, with strong pubescence and absent to weak anthocyanins.

5 Drawing Sheets

Latin name of the genus and species of the plant claimed: *Fragaria* x *ananassa.*

Variety denomination: 'PE-11.2175'.

BACKGROUND OF THE INVENTION

The present invention relates to a new and distinct strawberry variety named 'PE-11.2175'. This new variety is a result of a controlled cross made in 2011 in an ongoing breeding program between strawberry variety designated 'Red Glory' (not patented) as the seed (female) parent, and strawberry variety designated 'PS-5016' (U.S. Plant Pat. No. 17,312) as the pollen (male) parent. The variety is botanically known as *Fragaria* x *ananassa.*

The seedling resulting from the aforementioned cross was selected from a controlled breeding plot in Ventura County, Calif. in the fall of 2013. After its selection, the new variety was asexually propagated by stolons in Siskiyou and San Joaquin Counties, Calif. The new variety was tested extensively over the next several years in fruiting fields in Ventura County, Calif. This propagation has demonstrated that the combination of traits disclosed herein as characterizing the new variety are fixed and remain true-to-type through successive generations of asexual reproduction.

BRIEF SUMMARY OF THE INVENTION

'PE-11.2175' is primarily adapted to the climate and growing conditions of the central coast of California. The nearby Pacific Ocean provides the humidity and moderate temperatures needed to produce a strong, vigorous plant and maintain fruit quality during the fall production months.

The following traits have been repeatedly observed and are determined to be unique characteristics of 'PE-11.2175', which in combination distinguish this strawberry plant as a new and distinct variety:

1. Fruit is orange red in color, small in size, and conical in shape;
2. Fruit has fair flavor, medium to soft flesh, with seeds typically held below the surface;
3. Plant is large in size, semi-upright, with medium to dense density and strong vigor;
4. Foliage is medium to light green in color, large in size and slightly to strongly convex in cross section; and
5. Fruiting trusses are typically held beneath the foliage, with strong pubescence and absent to weak anthocyanins.

The strawberry variety that is believed to be most closely related to the new variety 'PE-11.2175' is 'PE-7.2059' (U.S. Plant Pat. No. 28,756). In side-by-side comparisons to the similar strawberry variety 'PE-7.2059', 'PE-11.2175' differs by the following combination of characteristics as described in Table 1.

TABLE 1

| Characteristic | 'PE-11.2175' | 'PE-7.2059' (U.S. Plant Pat. No. 28,756) |
|---|---|---|
| Fruit: color | Orange red | Red |
| Fruit: size | Small | Medium |
| Fruit: insertion of achenes | Below surface | Ranges from level with to above surface |
| Fruit: position of calyx attachment | Inserted | Ranges from level to raised |
| Fruit: firmness of flesh | Ranges from medium to soft | Medium |
| Plant: size | Large | Medium |
| Foliage: color | Ranges from medium green to light green | Medium green |
| Foliage: number of leaflets | 3 | 3-4 |
| Foliage: size | Large | Ranges from medium to small |
| Fruiting truss: position relative to foliage | Beneath | Level with |
| Disease: Fusarium wilt | Resistant | Susceptible |

For identification, a series of molecular markers have been determined for this new variety.

'PE-11.2175' differs from its parents, 'Red Glory' and 'PS-5016' by the following combination of characteristics as described in Tables 2 and 3.

TABLE 2

| Characteristic | 'PE-11.2175' | 'Red Glory' (not patented) |
|---|---|---|
| Fruit: color | Orange red | Red |
| Fruit: size | Small | Very small |
| Plant: size | Large | Medium |
| Plant: density | Ranges from medium to dense | Dense |

TABLE 3

| Characteristic | 'PE-11.2175' | 'PS-5016' (U.S. Plant Pat. No. 17,312) |
|---|---|---|
| Fruit: color | Orange red | Red |
| Fruit: insertion of achenes | Below surface | Level with surface |
| Fruit: flavor | Fair | Very good |
| Foliage: shape in cross section | Slightly to strongly convex | Slightly to strongly concave |
| Type of bearing: | Remontant | Not remontant |

BRIEF DESCRIPTIONS OF THE PHOTOGRAPHS

The accompanying color photographs illustrate the overall appearance of typical specimens of the new strawberry variety 'PE-11.2175' at various stages of development, as true as it is reasonably possible with color reproductions of this type. Color in the photographs may differ slightly from the color value cited in the botanical descriptions which accurately describe the color of 'PE-11.2175'. The depicted plant and plant parts of the new strawberry variety 'PE-11.2175' are approximately three to four months old. The photographs were taken in Ventura County, Calif.

DETAILED BOTANICAL DESCRIPTION

Figure 1:
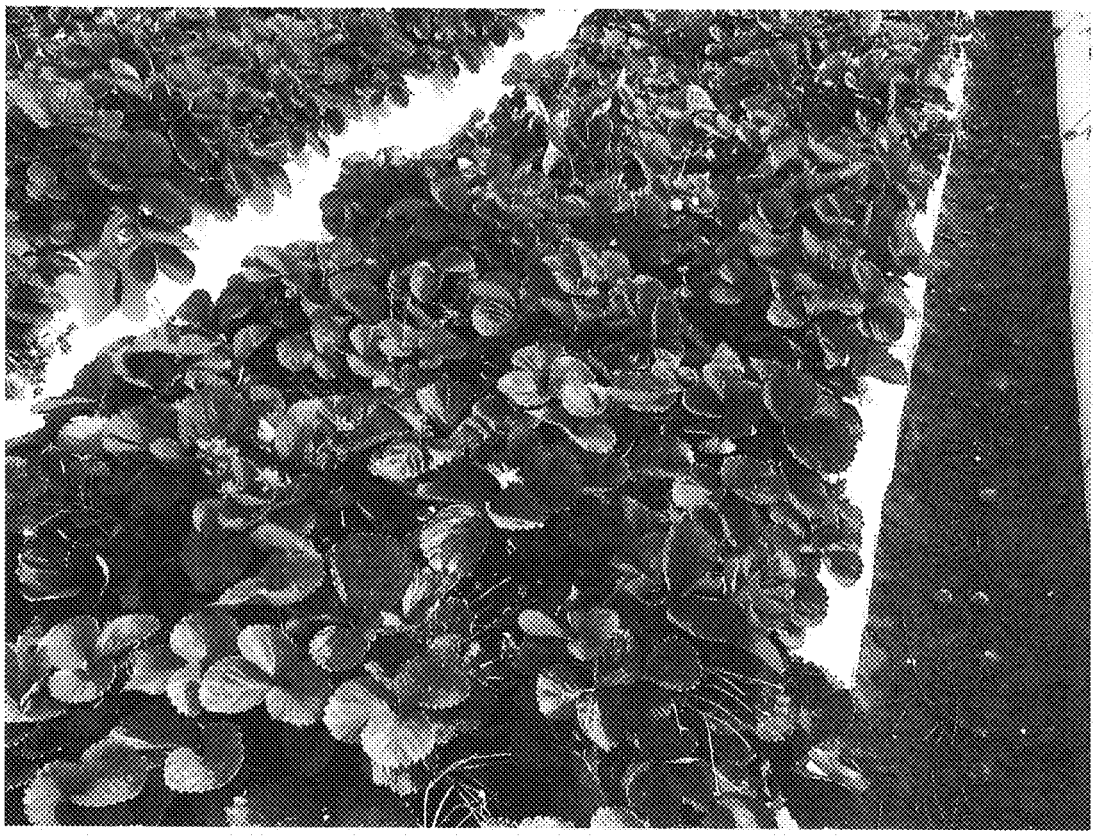
FIG. 1 shows fruiting field characteristics of 'PE-11.2175', taken in the month of November 2021.
Figure 2:
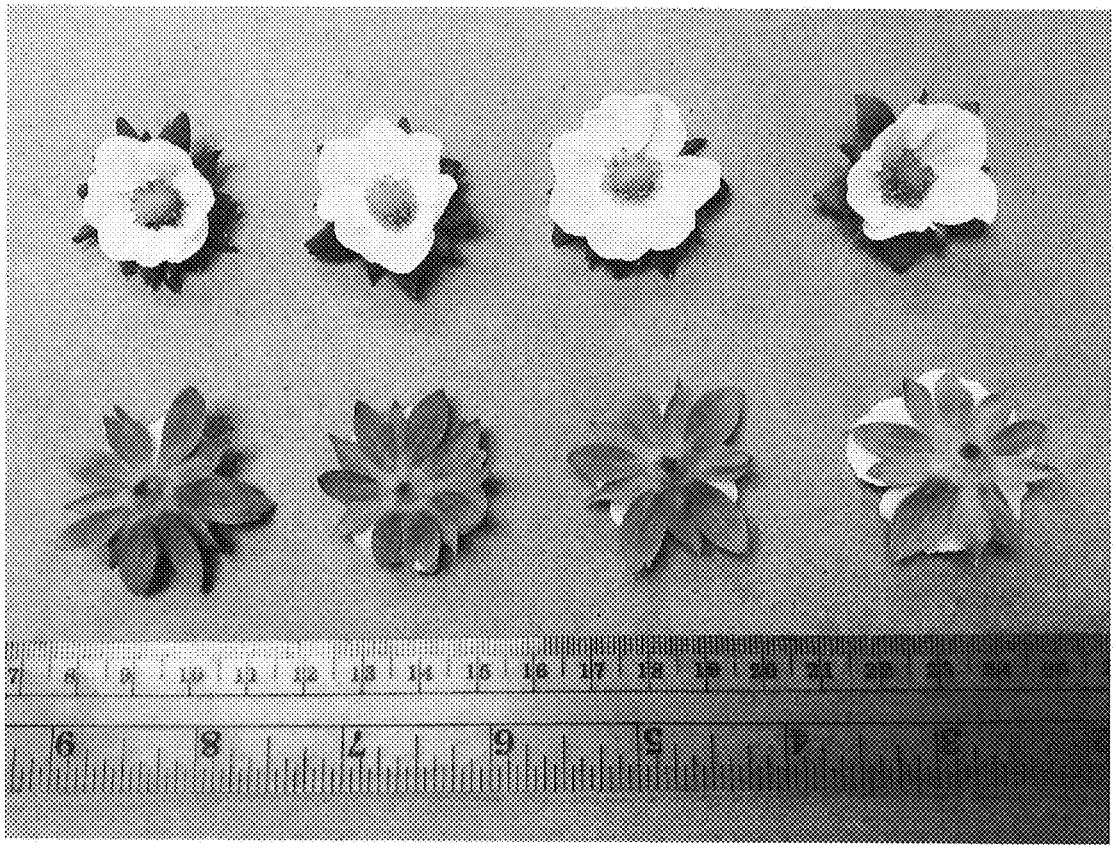
FIG. 2 shows upper and lower surfaces of flower and flower parts of 'PE-11.2175', taken in the month of October 2021.
Figure 3:
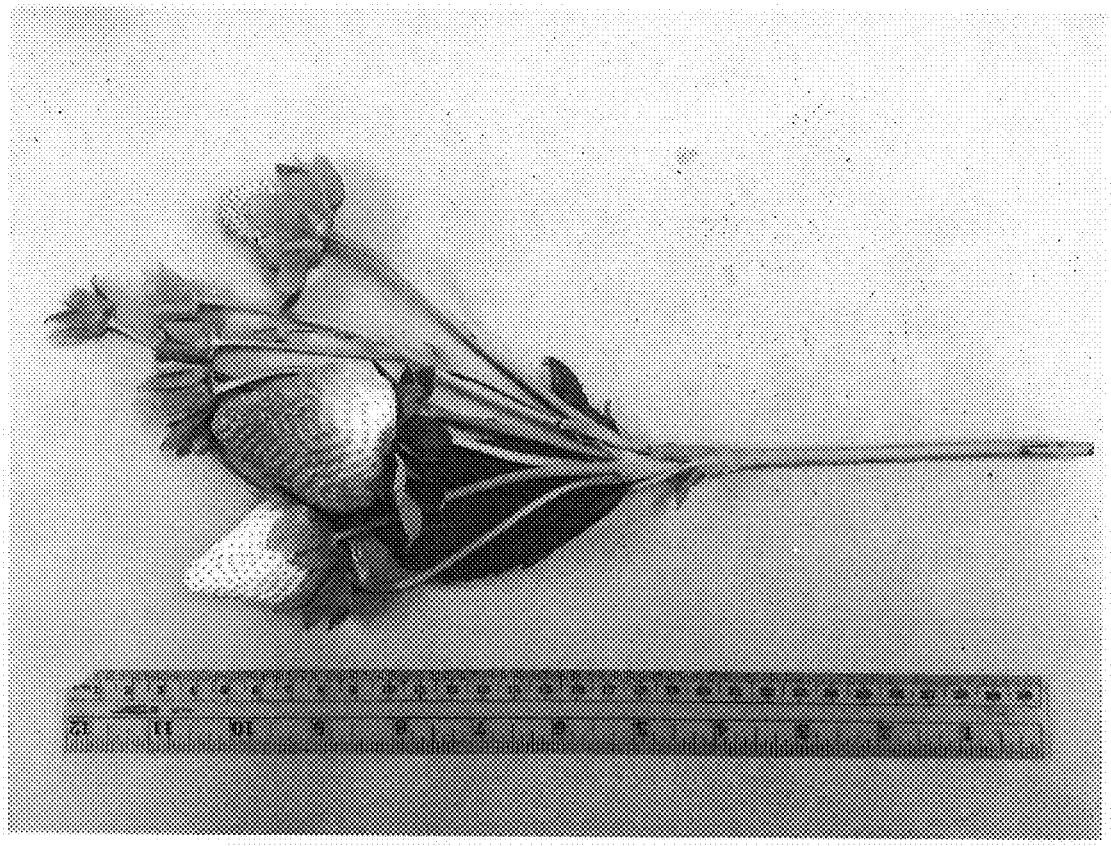
FIG. 3 shows typical fruiting truss and truss parts of 'PE-11.2175', taken in the month of November 2021.
Figure 4:
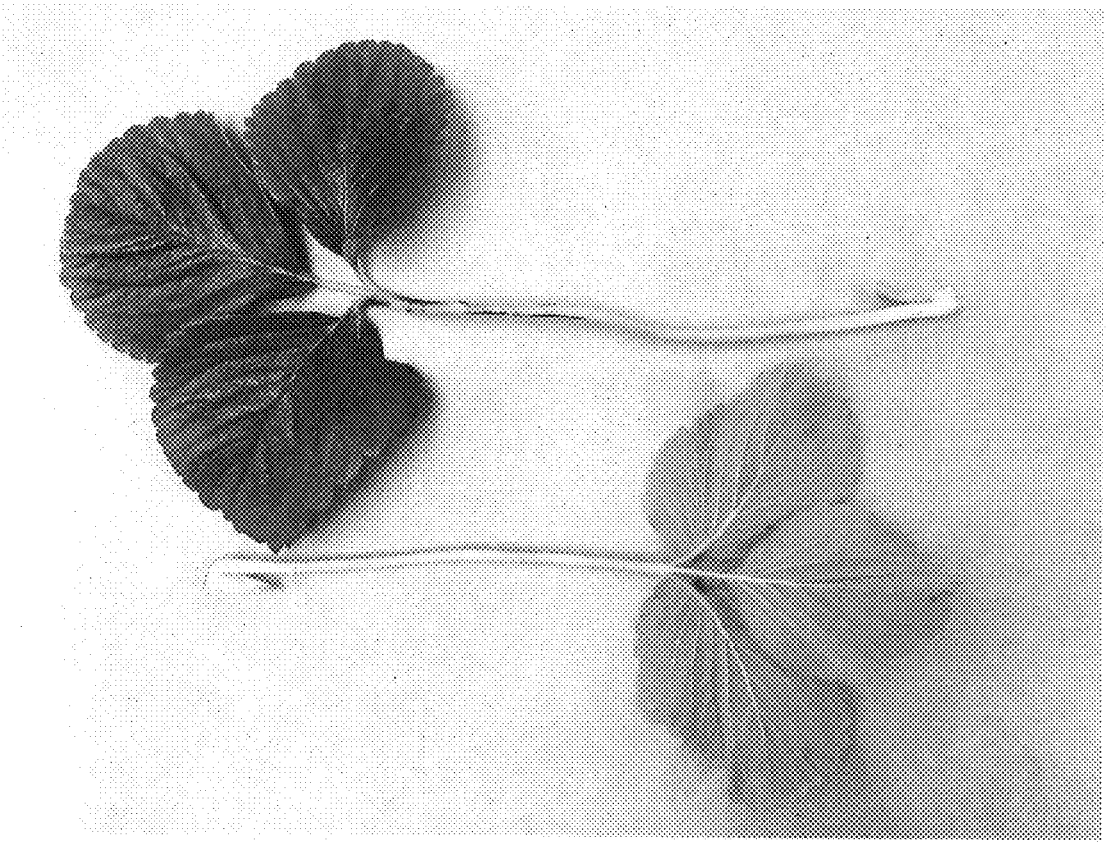
FIG. 4 shows upper and lower surfaces of leaf and leaf parts of 'PE-11.2175', taken in the month of November 2021.
Figure 5:
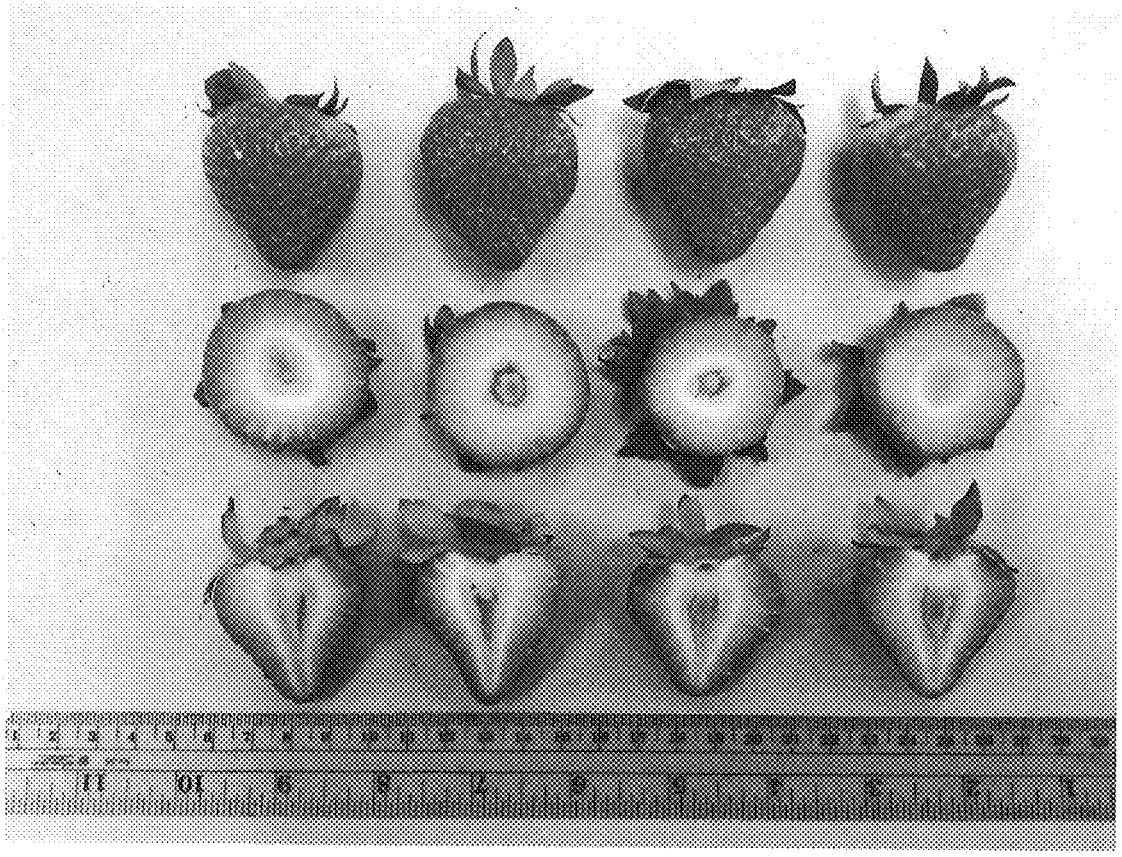
FIG. 5 shows internal and external mature fruit characteristics of 'PE-11.2175', taken in the month of November 2021.

The new variety 'PE-11.2175' has not been observed under all possible environmental conditions. The characteristics of the new variety 'PE-11.2175' may vary in detail, depending upon variations in environmental factors, including weather (temperature, humidity and light intensity), day length, soil type and location. In addition, the characteristics of any parental variety or comparison variety included in Tables 1, 2 and 3 of the present invention may vary in detail, depending upon variations in environmental factors, including weather (temperature, humidity and light intensity), day length, soil type and location.

The aforementioned photographs, together with the following description of the new variety 'PE-11.2175', unless otherwise noted, are based on observations taken during the 2021 growing season in Ventura County, Calif. These measurements and ratings were taken from plants of 'PE-11.2175' dug from a low-elevation nursery located in San Joaquin County, Calif. in January 2021 and planted approximately six months later in Ventura County, Calif. The approximate age of the observed plants is three to four months. Yield observations including average weight and marketable yield, along with fruit quality characteristics including soluble solids, are averaged from six years of data collected from the 2016 through 2021 growing seasons. Flower measurements and characteristics are from secondary flowers unless otherwise noted. Fruit characteristics and measurements are from secondary fruit, unless otherwise noted.

Where noted, color terminology follows The Royal Horticultural Society Colour Chart, London, Sixth Edition (2015).

The following characteristics describe fruit, plant, stolon, foliage, fruiting truss, flower, reproductive organs and pest and disease characteristics of the new strawberry 'PE-11.2175'.

Fruit characteristics:

*Color of mature fruit*.—RHS 43A (orange red).
*Color of internal flesh*.—RHS 43B (medium red).
*Color of core*.—RHS 43C (medium red).
*Average length* (*cm*).—3.9.
*Average width* (*cm*).—3.6.
*Size*.—Small.
*Average length/width ratio*.—1.08 (slightly longer than broad).
*Hollow center average length* (*mm*).—11.2.
*Hollow center average width* (*mm*).—3.1.
*Hollow center expression*.—Absent or very weak.
*Season average weight* (*gm*).—20.4.
*Marketable yield season* (*gm/plant*).—670.
*Predominant shape*.—Conical.

*Difference in shape between primary and secondary fruit*.—Slight.
*Band without achenes*.—Absent or very narrow.
*Evenness of surface*.—Even or very slightly uneven.
*Evenness of color*.—Even or very slightly uneven.
*Glossiness*.—Medium.
*Insertion of achenes*.—Below surface.
*Average calyx diameter* (*cm*).—4.8.
*Position of calyx attachment*.—Inserted.
*Attitude of sepals*.—Outward.
*Size of calyx in relation to fruit diameter*.—Slightly larger.
*Adherence of calyx* (*when fully ripe*).—Strong.
*Firmness of flesh*.—Ranges from soft to medium.
*Keeping quality*.—Fair.
*Fruit market*.—Fresh.
*Post-harvest fruit longevity* (*at* 1 *to* 3 *degrees Celsius*).—5 to 7 days.
*Distribution of red color of the flesh*.—Marginal and central.
*Flavor*.—Fair.
*Soluble solids* (% *brix*).—7.0.
*Achene color, shaded side*.—RHS 160A (greyed yellow group).
*Achene color, sun-exposed side*.—RHS 182A (greyed red group).
*Achene average length* (*mm*).—1.7.
*Achene average width* (*mm*).—0.7.
*Achene average weight* (*mg*).—0.57.
*Achene average quantity per berry*.—214.
*Achene shape*.—Elliptic.
*Flowering season* (50% *of plants with at least one flower*).—Early (August in Ventura County, Calif.).
*Maturing season* (50% *of plants with mature fruit*).—Early (October in Ventura County, Calif.).
*Flowering season*.—August to December (in Ventura County, Calif.).
*Harvest season*.—September to January (in Ventura County, Calif.).
*Harvest maturity*.—October (in Ventura County, Calif.).
*Plant hardiness*.—Zone 10 (USDA Plant Hardiness Zone Map).
*Type of bearing*.—Fully remontant (non-flowering runners).

Plant characteristics:
*Average height* (*cm*).—29.4.
*Average spread* (*cm*).—44.5.
*Size*.—Large.
*Habit*.—Semi-upright.
*Density*.—Ranges from medium to dense.
*Vigor*.—Strong.

Stolon characteristics:
*Color*.—RHS N144A (yellow green group).
*Anthocyanin coloration*.—RHS 182A (greyed red group).
*Anthocyanin intensity*.—Weak.
*Pubescence*.—Medium.
*Attitude of hairs*.—Upward.
*Average quantity in nursery* (*per square foot*).—6 to 7 (medium).
*Average diameter at first bract* (*mm*).—3.5 (medium).
*Length from mother plant to first daughter* (*cm*).—37.5.

Terminal leaflet characteristics:
*Average length* (*cm*).—9.3.
*Average width* (*cm*).—9.5.
*Average area terminal* ($cm^2$).—87.9.
*Average length/width ratio*.—0.98 (as long as broad).
*Shape of base*.—Obtuse.
*Shape of apex*.—Obtuse.
*Margins* (*shape of teeth*).—Rounded (crenate).
*Average serrations per leaf*.—25.3.

Foliage characteristics:
*Color of upper surface*.—RHS 137C (ranges from light green to medium green).
*Color of lower surface*.—RHS 147C (yellow green group).
*Color of venation, upper surface*.—RHS 137C (green group).
*Color of venation, lower surface*.—RHS 147D (yellow green group).
*Number of leaflets*.—3.
*Leaf size*.—Large.
*Average length* (*cm*).—14.5.
*Average width* (*cm*).—18.4.
*Average area foliage* ($cm^2$).—267.5.
*Shape in cross section*.—Slightly to strongly convex.
*Interveinal blistering*.—Strong.
*Texture of upper surface*.—Medium.
*Texture of lower surface*.—Smooth.
*Venation pattern*.—Pinnate reticulate.
*Leaf glossiness*.—Medium.
*Leaf variegation*.—Absent.

Petiole characteristics:
*Petiole color*.—RHS 145A (yellow green group).
*Petiole average length* (*cm*).—19.6.
*Petiole average diameter* (*mm*).—3.7.
*Attitude of hairs*.—Slightly outward.
*Frequency of bract leaflets*.—30% occurrence (occasionally).
*Size of bract leaflets*.—Medium.
*Pubescence*.—Ranges from moderate to sparse.
*Petiolule color*.—RHS 145A (yellow green group).
*Petiolule average length* (*mm*).—18.7.
*Petiolule average diameter* (*mm*).—2.0.

Stipule characteristics:
*Color*.—RHS 144B (yellow green group).
*Anthocyanin coloration*.—RHS 58A (red purple group).
*Anthocyanin intensity*.—Absent or very weak.
*Average length* (*mm*).—19.8.
*Average width* (*mm*).—10.4.
*Shape*.—Triangular.
*Texture*.—Light.
*Shape of base*.—N/A.
*Shape of apex*.—Acuminate.
*Margins*.—Entire (smooth).

Fruiting truss characteristics:
*Anthocyanin coloration*.—N/A.
*Anthocyanin intensity*.—Absent or very weak.
*Average length at maturity* (*cm*).—31.7.
*Position relative to foliage*.—Beneath.
*Flower quantity* (*season average per plant*).—43.0 (medium).
*Average fruit quantity per truss*.—10.5 (many).
*Attitude at first pick*.—Prostrate.
*Primary pedicel color*.—RHS 144B (yellow green group).

*Primary pedicel average length* (*cm*).—9.9.
*Primary pedicel average diameter* (*mm*).—3.3.
*Pedicel attitude of hairs*.—Upward.
*Pedicel texture*.—Weak.
*Primary peduncle color*.—RHS 144B (yellow green group).
*Primary peduncle average length* (*cm*).—11.0.
*Primary peduncle average diameter* (*mm*).—5.6.
*Peduncle texture*.—Strong.

Flower characteristics:
*Petal color, upper surface*.—RHS NN155C (white group).
*Petal color, lower surface*.—RHS NN155C (white group).
*Petal average length* (*mm*).—11.5.
*Petal average width* (*mm*).—12.1.
*Petal average length/width ratio*.—0.95 (as long as broad).
*Average petal quantity per flower*.—6.3.
*Petal shape*.—Obovate.
*Petal texture, upper surface*.—Smooth.
*Petal texture, lower surface*.—Smooth.
*Petal shape of base*.—Rounded.
*Petal shape of apex*.—Rotund.
*Petal margins*.—Entire (smooth).
*Sepal color, upper surface*.—RHS NN137A (green group).
*Sepal color, lower surface*.—RHS 138B (green group).
*Sepal average length* (*mm*).—13.8.
*Sepal average width* (*mm*).—5.9.
*Sepal average length/width ratio*.—2.35.
*Average sepal quantity per flower*.—12.6.
*Sepal shape*.—Ovate.
*Sepal texture, upper surface*.—Light.
*Sepal texture, lower surface*.—Light.
*Sepal shape of apex*.—Acute.
*Sepal margins*.—Entire (smooth).
*Corolla average diameter* (*mm*).—30.4 (medium).
*Flower average depth* (*mm*).—11.0 (medium).
*Calyx average diameter* (*mm*).—35.6.
*Size of calyx relative to corolla*.—Larger.
*Relative position of petals* (*flowers with* 5 *or* 6 *petals*).—Overlapping.
*Size of inner calyx relative to outer calyx*.—Smaller.

Reproductive organs:
*Anther color*.—RHS 13A (yellow orange group).
*Filament color*.—RHS 145C (yellow green group).
*Filament average length* (*mm*).—1.8.
*Anther average length* (*mm*).—0.8.
*Anther average width* (*mm*).—0.7.
*Anther shape*.—Elliptic.
*Pollen amount*.—Abundant.
*Ovary color*.—RHS 148C (yellow green group).
*Style color*.—RHS 151A (yellow green group).
*Pistil average quantity per flower*.—214.
*Pistil average length* (*mm*).—1.3.
*Style average length* (*mm*).—1.2.
*Stigma average diameter* (*mm*).—0.2.
*Stigma shape*.—Rounded.

Disease and pest reactions:
*Powdery mildew* (*sphaerotheca macularis*).—Moderately susceptible.
*Botrytis fruit rot* (*botrytis cinerea*).—Moderately susceptible.
*Fusarium wilt* (*fusarium oxysporum*).—Resistant.
*Two-spotted spider mite* (*tetranychus urticae*).—Moderately susceptible.

We claim:

1. A new and distinct strawberry plant named 'PE-11.2175', as herein described and illustrated by the characteristics set forth above.

* * * * *